United States Patent
Trauth et al.

(10) Patent No.: US 8,324,435 B2
(45) Date of Patent: Dec. 4, 2012

(54) PROCESS FOR THE MANUFACTURE OF NITRATED HYDROCARBONS

(75) Inventors: Daniel M. Trauth, Crystal Lake, IL (US); George D. Green, Cary, IL (US); Raymond J. Swedo, Mount Prospect, IL (US)

(73) Assignee: ANGUS Chemical Company

( * ) Notice: Subject to any disclaimer, the term of this patent is extended or adjusted under 35 U.S.C. 154(b) by 184 days.

(21) Appl. No.: 12/899,169

(22) Filed: Oct. 6, 2010

(65) Prior Publication Data

US 2011/0092750 A1    Apr. 21, 2011

Related U.S. Application Data

(60) Provisional application No. 61/253,143, filed on Oct. 20, 2009.

(51) Int. Cl.
  *C07C 205/00* (2006.01)

(52) U.S. Cl. ..................................................... 568/947

(58) Field of Classification Search .................... 568/947
See application file for complete search history.

(56) References Cited

U.S. PATENT DOCUMENTS

| | | | |
|---|---|---|---|
| 1,967,667 A | 7/1934 | Hass et al. |
| 2,071,122 A | 2/1937 | Hass et al. |
| 2,489,320 A | 11/1949 | Nygaard et al. |
| 3,689,576 A | 9/1972 | Bachman et al. |
| 4,469,904 A | 9/1984 | Wang et al. |
| 4,476,336 A | 10/1984 | Sherwin |
| 4,992,603 A | 2/1991 | Mari et al. |
| 2011/0028731 A1 | 2/2011 | Trauth et al. |
| 2011/0028732 A1 | 2/2011 | Trauth et al. |

OTHER PUBLICATIONS

Albright, "Nitration of Paraffins", Chemical Engineering, 1966, pp. 149-156.
International Search Report and Written Opinion for PCT/US2010/051619 dated Jan. 24, 2011.

*Primary Examiner* — Jafar Parsa

(57) ABSTRACT

Provided is a process for making nitrated hydrocarbons by reacting aqueous nitric acid with a hydrocarbon feedstock and a carboxylic acid under specific reaction conditions.

10 Claims, 1 Drawing Sheet

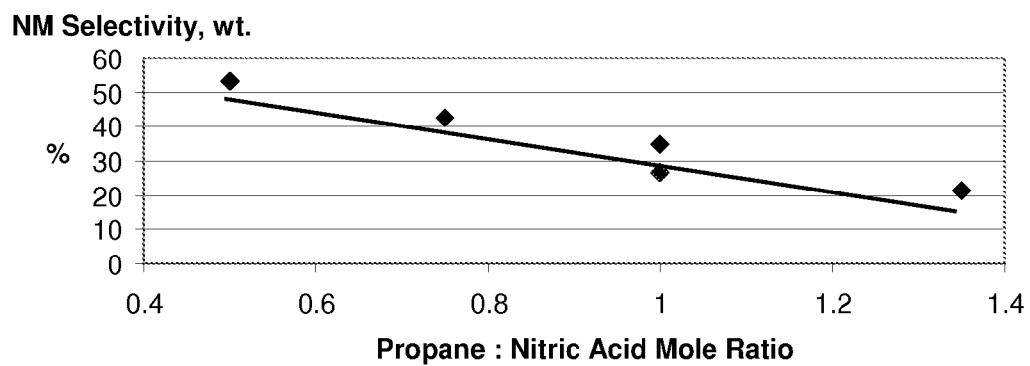

PROCESS FOR THE MANUFACTURE OF NITRATED HYDROCARBONS

This application claims priority to U.S. provisional application Ser. No. 61/253,143, filed Oct. 20, 2009, which is incorporated herein by reference in its entirety.

FIELD OF THE INVENTION

The invention relates to a process for making nitrated hydrocarbons. The process comprises reacting aqueous nitric acid with a hydrocarbon feedstock and a carboxylic acid under specific reaction conditions.

BACKGROUND OF THE INVENTION

The nitration of hydrocarbons generally produces a variety of products depending upon the reaction conditions and the feedstock structure. For instance, the commercial vapor phase process for propane nitration results in a mixture of four nitroalkane products (nitromethane, 1-nitropropane, 2-nitropropane, and nitroethane) in essentially fixed relative concentrations. Certain nitrated hydrocarbon products, however, may be more desirable than others and the desirability of particular products may change as commercial supply and demand conditions change. It has been a long-time goal, therefore, to selectively produce the more desirable nitrated compounds at the expense of the less desirable compounds.

In contrast to commercial vapor phase nitration, the mixed vapor-liquid phase or high pressure nitration of propane has been postulated in the past to be a technique by which 2-nitropropane, often a more desirable nitrated hydrocarbon, can be potentially produced without making other less desirable nitro compounds typically formed during vapor-phase nitration. See e.g., U.S. Pat. No. 2,489,320 (Nygaard et al.) and Albright, L. F., "Nitration of Paraffins", Chem. Engr., (1966) pp. 149-156.

Despite the initial optimism, the prior art technology for nitrating propane in the mixed vapor-liquid phase was never practical for a number of reasons, including because the conversion of nitric acid is low, the nitric acid is not readily recoverable, problems with reactor corrosion by the nitric acid, and difficulty in controlling reaction exotherm.

Obtaining a high yield of desirable nitrated hydrocarbon(s) is an important economic factor to be considered since low yields necessitate the use of more feed and therefore result in higher costs. Furthermore, when nitric acid is used as the nitrating agent, the unreacted nitric acid becomes a waste product and costs are incurred to dispose of waste products properly. High conversion of the reactant hydrocarbon (to nitrated hydrocarbons) is also economically important in order to minimize capital and energy expenses associated with the purification and recycling of unreacted reactants.

It would be a significant advance in the field, therefore, to provide more economical, selective, and environmentally friendly processes for the manufacture of desirable nitrated hydrocarbons.

BRIEF SUMMARY OF THE INVENTION

The invention provides a mixed liquid-vapor phase process for making a nitrated hydrocarbon composition containing two or more compounds of formula I:

$$R-NO_2 \quad (I)$$

The process comprises: (a) forming a reaction mixture comprising a hydrocarbon feedstock and an aqueous feed, wherein the aqueous feed comprises water, between about 10 and about 50 weight percent of nitric acid, and at least about 15 weight percent of a carboxylic acid of formula II;

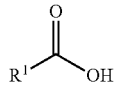

(II)

and (b) reacting the mixture at a reaction pressure and a reaction temperature to provide a product stream comprising the nitrated hydrocarbon composition. The groups R and $R^1$ are as defined herein.

DESCRIPTION OF THE FIGURES

FIG. 1 is a graph showing nitromethane selectivity as a function of propane to nitric acid mole ratio, according to one embodiment of the invention.

DETAILED DESCRIPTION OF THE INVENTION

As noted above, the invention provides a mixed liquid-vapor phase process for making a nitrated hydrocarbon composition. The selection of temperature, pressure, the nitric acid dilution level, together with the appropriate selection of hydrocarbon feedstock and carboxylic acid starting materials, as taught herein, provides a nitration process that is significantly improved over prior art processes.

For instance, it has been surprisingly found that the nitration of the hydrocarbon feedstock and carboxylic acid together, under the conditions described herein, performs in a manner that is better than would be expected based on the individual performance of the hydrocarbon feedstock and carboxylic acid when nitrated separately. In particular, it is observed that both the efficiency of the reaction and the selectivity for desirable nitrated hydrocarbons is greater than would otherwise be predicted.

This surprising improvement in efficiency and selectivity advantageously permits nitrated hydrocarbons to be manufactured in a cost effective manner, and with less environmental impact. In addition, the ability to efficiently target the selective formation of particular nitrated hydrocarbons provides a process that can more readily align to commercial supply and demand conditions. For instance, if there is increased commercial demand for nitromethane, the process of the invention can be adjusted to favor the formation of more nitromethane in a nitrated hydrocarbon product mixture. As a consequence, costs associated with storage or disposal of over-manufactured materials can be significantly mitigated.

The process of the invention comprises:
(a) forming a reaction mixture comprising a hydrocarbon feedstock and an aqueous feed, wherein the aqueous feed comprises water, between about 10 and about 50 weight percent of nitric acid, and at least about 15 weight percent of a carboxylic acid of formula II;

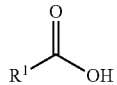

(II)

wherein $R^1$ is $C_1$-$C_{12}$ alkyl or $C_3$-$C_{12}$ cycloalkyl; and
(b) reacting the mixture at a reaction pressure and a reaction temperature to provide a product stream comprising the nitrated hydrocarbon composition.

The hydrocarbon feedstock may include, without limitation, one or more of the following: alkanes and cycloalkanes (including alkyl substituted cycloalkanes), such as propane, isobutane, n-butane, isopentane, n-pentane, n-hexane, n-heptane, n-octane, 2,3-dimethylbutane, cyclohexane, cyclopentane, and methylcyclohexane; aryl alkanes such as ethylbenzene, toluene, xylenes, isopropyl benzene; 1-methylnaphthalene and 2-methylnaphthalene and 4-methylbiphenyl; fused cycloalkanes; alkyl substituted fused aryl compounds; and fused cycloalkane-aryl compounds (including alkyl substituted derivatives), such as tetralin, decalin, and methylnaphthalene. The nitration of reactants that already have one or more nitro substituents is also contemplated provided that the reactant still has an available hydrogen.

In some embodiments, the hydrocarbon feedstock is a $C_3$-$C_{12}$ alkane (including a linear or branched material) or a $C_3$-$C_{12}$ cycloalkane (including alkyl substituted cycloalkane). In some embodiments, the alkane or cycloalkane contains 3 to 10 carbon atoms, alternatively 3 to 8 carbon atoms, alternatively 3 to 6 carbon atoms. Examples of suitable $C_3$-$C_{12}$ alkane and $C_3$-$C_{12}$ cycloalkane include, but are not limited to, n-decane, n-hexane, cyclohexane, n-pentane, cyclopentane, n-butane, iso-butane, or propane. In some embodiments, propane is preferred.

In the process of the invention, the carboxylic acid of formula II reacts with the nitric acid to form a nitrated hydrocarbon. The acid portion of the molecule also undergoes cleavage during the process. The carboxylic acid is selected based on which particular nitrated hydrocarbon it is desired to enrich in the nitrated hydrocarbon product mixture of the overall process. Thus, for example, acetic acid results in increased formation of nitromethane, propionic acid in nitroethane, etc.

Carboxylic acids for use in the invention are generally of formula II as shown above. The $R^1$ group of the formula II compound may be linear or branched $C_1$-$C_{12}$ alkyl or it may be $C_3$-$C_{12}$ cycloalkyl (including alkyl substituted cycloalkyl). In some embodiments, $R^1$ is $C_1$-$C_{10}$ alkyl, alternatively $C_1$-$C_8$ alkyl, alternatively $C_1$-$C_5$ alkyl, alternatively $C_4$-$C_7$ cycloalkyl. Examples of suitable carboxylic acids of formula II include, but are not limited to, acetic acid, propanoic acid, butanoic acid, hexanoic acid, and 1-cyclohexylacetic acid.

According to the invention, the carboxylic acid of formula II comprises at least about 15 weight percent, alternatively at least about 25 weight percent, alternatively at least about 35 weight percent, alternatively at least about 40 weight percent, alternatively at least about 50 weight percent, or alternatively at least about 55 weight percent, of the process's aqueous feed (water, nitric acid, and carboxylic acid). In some embodiments, the carboxylic acid comprises no more than about 75 weight percent, alternatively no more than about 65 weight percent, of the aqueous feed.

The product stream of the process can contain carboxylic acids, which may be formed by the oxidation of the hydrocarbon feedstock and/or are the result of unconsumed starting material. According to some embodiments of the invention, at least a portion of the carboxylic acids of the product stream can be recycled and used as the carboxylic acid of formula II of the feed stream. The carboxylic acid can be isolated from the product stream using techniques well known to those skilled in the art, including distillation, liquid-liquid extraction followed by distillation, azeotropic distillation, membrane permeation, and aqueous extraction. Such recycling of product stream components results in the reduction of waste material.

In some embodiments, the carboxylic acid of formula II can be generated in-situ through the reaction of a precursor, such as an alcohol or an aldehyde, with the nitric acid. For instance, ethanol or acetaldehyde can be used for in-situ formation of acetic acid, or 1-butanol can be used for in-situ formation of butyric acid.

The nitric acid of the process of the invention is used at a concentration of least about 10 weight percent based on the total weight of the aqueous feed (water, nitric acid, and carboxylic acid). In some embodiments, the nitric acid concentration is least about 15 weight percent, alternatively at least about 20 weight percent, or alternatively at least about 30 weight percent. Further, the concentration is no more than about 50 weight percent. In some embodiments, the nitric acid concentration is no more than about 40 weight percent, or alternatively no more than about 35 weight percent. In further embodiments, the nitric acid concentration is between about 15 and about 40 weight percent. In other embodiments, the nitric acid concentration is between about 18 and about 35 weight percent.

The process is carried out in a reactor that is preferably made or lined with a corrosion resistant material, such as titanium. The reactor is optionally surrounded by a shell with input and output ports for feeding a heat transfer fluid. The heat transfer fluid, which can be for example an oil, allows the temperature of the reaction to be controlled to within the desired parameters.

It should be noted, however, that because the reaction between the nitric acid and the hydrocarbon feedstock/carboxylic acid is exothermic, use of a shell and a heat transfer fluid are not required. The temperature of the reaction can be regulated to be within the desired parameters by simply regulating the addition rate and/or concentration of the reactants.

In some embodiments, the reactor is operated in a downflow mode. That is, the reactor, which is preferably of an elongated and linear shape, such as a tube, is positioned so that reactants are added through an entry port at or near the top of the reactor and then flowed down the reactor for sufficient residence time to allow reaction to occur and formation of the product stream containing the nitrated hydrocarbon composition. The product stream is collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

The reactor is optionally packed with a packing material to improve reactant mixing and heat transfer. The packing can also be used for varying the reactor volume. Suitable packing materials include, for example, glass beads, random packing, or structured packing, such as those typically employed in distillation devices. Other packing materials are known in the art and may be used.

The hydrocarbon feedstock, carboxylic acid of formula II, and nitric acid and water can be mixed, or partially mixed, prior to entry into the reactor or, alternatively, they can be added individually, with mixing to occur within the reactor. Further, one or more of the reactants and water, whether added together or individually, can be preheated prior to entry into the reactor. In some embodiments, the mole ratio of hydrocarbon feedstock to nitric acid is at least about 0.3:1, alternatively at least about 0.4:1, alternatively at least about 0.5:1. In some embodiments, the mole ratio of hydrocarbon feedstock is 0.8:1 or less, alternatively 0.7:1 or less, or alternatively 0.6:1 or less.

The reaction temperature within the reactor may be controlled (for example with heat exchange fluid or using heat generated from the reaction) to greater than about 140 degrees Celsius and less than about 325 degrees Celsius. In other embodiments, the temperature may be greater than about 215 degrees Celsius and less than about 325 degrees Celsius. In some embodiments, the temperature may be greater than about 180 degrees, greater than about 200 degrees, greater than about 230 degrees, or greater than about 240 degrees. In further embodiments, the temperature may be less than about 290 degrees, less about 280 degrees, less than about 270 degrees, or less than about 250 degrees. In other embodiments, the temperature may be between about 200 and 250 degrees Celsius. In yet further embodiments, the temperature may be between about 215 and 280 degrees Celsius, or between about 220 and 270 degrees Celsius.

The pressure in the reactor should be maintained at least about 500 psi (34 atm), preferably at least about 1000 psi (68 atm), and more preferably at least about 1200 psi (82 atm). Further, the pressure may be less than about 1600 psi (109 atm), preferably less than about 1500 psi (102 atm), and more preferably less than about 1400 psi (95 atm). In other embodiments, the pressure may between about 1000 psi (68 atm) and 1400 psi (95 atm). Various methods known in the art may be used for maintaining the pressure within the desired range including, for example, through the use of a back-pressure regulator.

The residence time of the reactants in the reactor is preferably at least about 30 seconds, more preferably at least about 90 seconds. Residence time can be controlled in various ways including, for example, by the length and/or width of the reactor or through the use of packing material. Residence time is determined by dividing the volume of the reactor by the inlet flow rates. Following sufficient residence time, the nitration products are collected from the reactor through the reactor's exit port.

The process of the invention results in the nitration of the hydrocarbon feedstock/carboxylic acid mixture. That is, compounds are formed in which at least one of the hydrogen atoms of the reactant hydrocarbon and at least one of the hydrogen atoms of the carboxylic acid are replaced with a nitro group $NO_2$ (in addition, as noted, the acid moiety of the carboxylic acid is cleaved). Additional hydrogen atoms on each compound may optionally be replaced with further nitro groups, resulting in the formation of, for example, dinitro-compounds. As a consequence, the nitrated hydrocarbon composition that forms in the process comprises a mixture of nitrated hydrocarbons. One or more of the nitrated hydrocarbons may be separated from the product stream and/or further purified by known techniques, such as distillation, pervaporation, or membrane separation.

As noted, the nitrated hydrocarbon composition formed in the process of the invention comprises a mixture of nitrated compounds. In particular, the composition comprises two or more compounds of the formula I:

$$R-NO_2 \quad (I)$$

wherein R is independently in each compound a hydrocarbon group containing 1-12 carbon atoms. Examples of hydrocarbon groups include, without limitation, alkyl (linear or branched), cycloalkyl (including alkyl substituted cycloalkyl), fused cycloalkyl; alkyl substituted aryl; and fused cycloalkyl-aryl (including alkyl substituted derivatives). The hydrocarbon may optionally be substituted with 1 or 2 additional nitro groups.

In some embodiments, the R group may be linear or branched $C_1$-$C_{12}$ alkyl or it may be $C_3$-$C_{12}$ cycloalkyl (including alkyl substituted cycloalkyl). In some embodiments, R is $C_1$-$C_{10}$ alkyl, alternatively $C_1$-$C_8$ alkyl, alternatively $C_{10}C_5$ alkyl, or alternatively $C_4$-$C_7$ cycloalkyl, each being optionally substituted with 1 or 2 additional nitro groups (in addition to the nitro group already present in the formula I compound).

Examples of formula I compounds include, but are not limited to, nitromethane, nitroethane, nitropropanes (e.g., 1-nitropropane, 2-nitropropane, 2,2-dinitropropane), nitrobutanes (e.g., 1-nitrobutane, 2-nitrobutane), 2-methyl-2-nitropropane, nitropentanes (e.g., 1-nitropentane, 2-nitropentane, 3-nitropentane), nitrohexanes (e.g., 1-nitrohexane, 2-nitrohexane, 3-nitrohexane), nitrocyclohexane, nitroheptanes (e.g., 1-nitroheptane, 2-nitroheptane, 3-nitroheptane, 4-nitroheptane), nitrooctanes (e.g., 1-nitrooctane, 2-nitrooctane, 3-nitrooctane, 4-nitrooctane), nitrononanes (e.g., 1-nitrononane, 2-nitrononane, 3-nitrononane, 4-nitrononane, 5-nitrononane), and nitrodecanes (e.g., 1-nitrodecane, 2-nitrodecane, 3-nitrodecane, 4-nitrodecane, 5-nitrodecane).

In an exemplary embodiment, the process of the invention is used to form a nitrated hydrocarbon composition comprising a mixture of 2-nitropropane and nitromethane. The process of this exemplary embodiment comprises:
  (a) forming a reaction mixture comprising propane and an aqueous feed comprising water, between about 10 and about 50 weight percent of nitric acid, and at least about 15 weight percent of acetic acid; and
  (b) reacting the mixture at a pressure of at least about 1000 psi and a temperature of between about 180 and about 325 degrees Celsius to provide a product stream comprising the nitrated hydrocarbon composition. One or more of the nitrated hydrocarbons may be separated from the product stream.

In this embodiment, the nitrated hydrocarbon composition contains at least nitromethane, and 2-nitropropane, and may also contain nitroethane, 1-nitropropane, and/or 2,2-dinitropropane. The embodiment is particularly useful for forming a nitrated hydrocarbon composition that is enriched in nitromethane and/or 2-nitropropane, both highly desirable nitrated hydrocarbons. Prior art processes have not been able to provide these materials in a single process with the selectivity and efficiency demonstrated by the invention. As shown by the examples, the process of this embodiment is capable of providing a nitrated hydrocarbon composition that comprises nitromethane at a selectivity of 67 mole percent and 2-nitropropane at a selectivity of 28 mole percent (see Example 1C). In addition, the process is capable of providing an efficiency (measured as conversion of consumed starting materials to nitrated hydrocarbons as opposed to other undesired byproducts, such as oxidation byproducts) of greater than 90%.

In some embodiments of the foregoing exemplary embodiment, the acetic acid comprises at least about 25 weight percent, alternatively at least about 35 weight percent, alternatively at least about 40 weight percent, alternatively at least about 50 weight percent, or alternatively at least about 55 weight percent of the aqueous feed (water, nitric acid, and acetic acid). In some embodiments, the acetic acid comprises no more than about 75 weight percent, alternatively no more than about 65 weight percent.

In some embodiments of the foregoing exemplary embodiment, the mole ratio of propane to nitric acid is between about 0.3:1 and about 0.7:1, alternatively it is between about 0.4:1 and about 0.6:1.

In some embodiments of the foregoing exemplary embodiment, the reaction pressure is at least about 1000 psi (68 atm), preferably at least about 1200 psi (82 atm). Further preferably, the pressure is about 1600 psi (109 atm) or less, preferably about 1500 psi (102 atm) or less, more preferably about 1400 psi (95 atm) or less. In further embodiments, the pressure is between about 1300 psi (88 atm) and 1500 psi (102 atm).

In some embodiments of the foregoing exemplary embodiment, the temperature of the reaction is at least about 215 degrees, at least about 220 degrees, at least about 230 degrees or at least about 240 degrees. In further embodiments, the temperature is no more than about 290 degrees, no more than about 280 degrees, or no more than about 270 degrees. In other embodiments, the temperature is between about 215 and 280 degrees Celsius, or between about 220 and 270 degrees Celsius. In further embodiments, the temperature is between about 220 and 250° C., alternatively between about 230 and 240° C.

The nitrated hydrocarbon compounds prepared by the process of the invention are useful in a wide variety of applications including, for instance, as starting materials in the synthesis of pharmaceutical compounds, neutralizing agents, hardening agents, and a variety of other uses.

The following examples are illustrative of the invention but are not intended to limit its scope. Unless otherwise indicated, the ratios, percentages, parts, and the like used herein are by weight.

EXAMPLES

General. Various aspects of the invention are demonstrated using a lab scale reactor. The reactor is a single tube shell-and-tube heat exchanger with a thermowell located axially down the center of the reactor in order to determine the temperature profile along the reactor's length. The reactor is 46" long and has a shell which is 1.25" OD 304 stainless steel with a ½" OD (0.37" ID) type 2 titanium process tubing and a ⅛" OD (0.093" ID) type 2 titanium thermowell. A very fine, movable thermocouple is inserted into the thermowell for the temperature profile measurement. The thermowell can be removed and the reactor filled with packing. The reactor is mounted vertically. The nitric acid and propane reactant streams are mixed in a Swagelok "T" at room temperature prior to entering the reactor. Hot oil used is fed to the reactor shell countercurrent to the reactants. The reactor effluent is cooled in a shell-and-tube heat exchanger using city water as the coolant. The effluent is then depressurized with the gases and liquids collected, measured, and analyzed.

In the examples below, the mass balance of the nitration reaction is determined by GC/MS for gases, aqueous, nitroalkane oil, and scrubber liquids, Karl Fisher titration for water content, potentiometric titration for strong/weak acid quantification, and HPLC for weak acid identification and quantification.

Metrics shown in the Tables below are calculated as follows:

Nitric Acid conversion (%)=100×(g Nitric Acid in–g Nitric Acid out)/g Nitric Acid in;

Hydrocarbon feedstock conversion (%)=100×(g hydrocarbon feedstock in–g hydrocarbon feedstock out)/g hydrocarbon feedstock in;

Moles of hydrocarbon feedstock consumed=(g hydrocarbon feedstock in–g hydrocarbon feedstock out)/mol wt of hydrocarbon feedstock;

Moles of carboxylic acid consumed=(g carboxylic acid in–g carboxylic acid out)/mol wt of carboxylic acid;

Mole % conversion to nitrated hydrocarbons=total moles of nitrated hydrocarbons formed/(moles of hydrocarbon feedstock consumed+moles of carboxylic acid consumed);

Total moles of nitrated hydrocarbons formed (in the propane example)=moles nitromethane+moles nitroethane+moles nitropropanes+moles dinitropropane;

Mole % selectivity for nitromethane=moles nitromethane/total moles nitrated hydrocarbons formed;

Mole % selectivity for nitroethane=moles nitroethane/total moles nitrated hydrocarbons formed;

Mole % selectivity for 1-nitropropane=moles 1-nitropropane/total moles nitrated hydrocarbons formed;

Mole % selectivity for 2-nitropropane=moles 2-nitropropane/total moles nitrated hydrocarbons formed;

Carboxylic acid concentration=g carboxylic acid in/(g carboxylic acid in+g nitric acid in+g water in).

Example 1

Nitration of Propane, Acetic Acid, and Combinations

This Example compares the nitration reactions of propane alone (comparative example), acetic acid alone (comparative example), and combinations of propane and acetic acid (inventive example). The Example demonstrates the increased conversion of starting materials to nitrated hydrocarbon products as well the enhanced selectivity for nitromethane using the process of the invention. Both the increased conversion and the enhanced selectivity are greater than would be expected based on the performance of the comparative examples.

Comparative Example 1A

Nitration of Propane

Propane is nitrated using dilute aqueous nitric acid as the nitrating agent with the above-described reactor at the following process conditions: 1400 psi reactor pressure, 235° C. hot oil temperature, 1.35:1 propane to nitric acid mole ratio, 29.8 wt. % nitric acid strength (in water), and 120 second residence time (based on the volume of the reactor divided by the flow rate of the feeds at room temperature and 1400 psi). The results of the mass balance are shown in Table 1. Performance metrics are compared in Table 4 below.

TABLE 1

Mass balance for nitration of propane

| Component | Feed (g) | Effluent (g) |
|---|---|---|
| Propane | 570 | 339 |
| Nitric Acid | 604 | 73.4 |
| Water[1] | 2538 | 2768 |
| Acetic Acid | 0 | 73.6 |
| Acetone | 0 | 1.8 |
| Nitromethane | 0 | 4.1 |
| Nitroethane | 0 | 2.0 |
| 2-Nitropropane | 0 | 221 |
| 1-Nitropropane | 0 | 33.9 |
| 2,2-Dinitropropane | 0 | 3.7 |
| Nitric Oxide | 0 | 123 |
| Nitrous Oxide | 0 | 12.1 |
| Nitrogen | 0 | 14.5 |
| Carbon Monoxide | 0 | 23.4 |
| Carbon Dioxide | 0 | 56.7 |

[1]Water in versus water out includes water used to scrub the off-gas from the reactor.

Comparative Example 1B

Nitration of Acetic Acid

Acetic acid is nitrated at the following process conditions: 1400 psi reactor pressure, 235° C. hot oil temperature, 2:1 acetic acid to nitric acid mole ratio, 30 wt. % nitric acid strength (in water), and 180 second residence time. The aqueous feed composition is 30 wt. % nitric acid, 57.1 wt. % acetic acid, and 12.9 wt. % water. The results of the mass balance are shown in Table 2. Performance metrics are compared in Table 4 below.

TABLE 2

Mass balance for nitration of acetic acid

| Component | Feed (g) | Effluent (g) |
|---|---|---|
| Propane | 0 | 0 |
| Nitric Acid | 440 | 331 |
| Water | 189 | 210 |
| Acetic Acid | 839 | 777 |
| Acetone | 0 | 0 |
| Nitromethane | 0 | 18.6 |
| Nitroethane | 0 | 0 |
| 2-Nitropropane | 0 | 0 |
| 1-Nitropropane | 0 | 0 |
| 2,2-Dinitropropane | 0 | 0 |
| Nitric Oxide | 0 | 25.7 |
| Nitrous Oxide | 0 | 4.7 |
| Nitrogen | 0 | 6.2 |
| Carbon Monoxide | 0 | 6.6 |
| Carbon Dioxide | 0 | 82.3 |

Inventive Example 1C

Nitration of Propane and Acetic Acid

Process conditions: reactor pressure of 1700 psig; hot oil temperature of 235° C.; propane-nitric acid mole ratio of 0.47:1; residence time of 90 seconds based on reactor volume/feed volume at room temperature and 1700 psig; nitric acid strength of 30 weight percent. The aqueous feed composition contains: 30 wt. % nitric acid, 57.1 wt. % acetic acid, and 12.9 wt. % water. The results of the mass balance for the reaction are shown in Table 3. Performance metrics are compared in Table 4 below.

TABLE 3

Mass balance for nitration of propane/acetic acid

| Component | Feed (g) | Effluent (g) |
|---|---|---|
| Propane | 158 | 83.4 |
| Nitric Acid | 483 | 1.3 |
| Water | 207 | 286 |
| Acetic Acid | 920 | 750 |
| Acetone | 0 | 7.9 |
| Nitromethane | 0 | 172 |
| Nitroethane | 0 | 2.1 |
| 2-Nitropropane | 0 | 106 |
| 1-Nitropropane | 0 | 13.7 |
| 2,2-Dinitropropane | 0 | 1.2 |
| Nitric Oxide | 0 | 51.4 |
| Nitrous Oxide | 0 | 6.7 |
| Nitrogen | 0 | 18.7 |
| Carbon Monoxide | 0 | 29.1 |
| Carbon Dioxide | 0 | 138 |

As can be seen from Table 4, nitration of propane alone results in a mole percent conversion to nitrated hydrocarbons of 57% and selectivity for nitromethane of only 2.3% (comparative example 1A). Nitration of acetic acid alone, while expectedly providing nitromethane as the only nitrated alkane, nevertheless exhibited a very poor mole conversion of only 30% (comparative Example 1B). In contrast, mole conversion to nitrated hydrocarbons with inventive Example 1C is 92%, greater than would be expected based on the performance of propane alone or acetic acid alone. In addition, the selectivity for nitromethane of 67%, coupled with the better conversion rate (92%), allows for the production of nitromethane with greater efficiency than would be expected from the performance of the acetic acid and propane acting alone. As is also evident from Table 4, the percent nitric acid and propane conversion is superior with inventive Example 1C.

Example 2

Effect of Reaction Temperature on Nitromethane Selectivity

This example demonstrates the effect of reaction temperature on nitrated hydrocarbon selectivity. Three runs are made at varying reaction temperature using the following conditions: propane-nitric acid mole ratio of 1.35:1; nitric acid concentration of 30 wt. %; acetic acid concentration of 57 wt. %; pressure of 1400 psig; and residence time of 2 minute. The tested temperatures (hot oil temperature) are 180, 200, and 235° C. Results are shown in Table 5.

As demonstrated in Table 5, nitromethane selectivity is observed to increase with increasing reactor temperature, whereas 2-nitropropane selectivity remains essentially constant with all three temperatures.

TABLE 5

| Temperature (° C.) | Mole % selectivity for nitro-methane | Mole % selectivity for 2-nitro-propane |
|---|---|---|
| 180 | 11.2 | 78.6 |
| 200 | 15.8 | 74.3 |
| 235 | 28.0 | 61.9 |

Example 3

Effect of Acetic Acid Concentration

This Example demonstrate the effect of acetic acid concentration on nitrated hydrocarbon selectivity. Three runs are made at varying acetic acid concentration using the following

TABLE 4

Summary of various performance metrics.

| Ex.* | Propane | Acetic Acid | ° C. | psi | Propane/ nitric ratio | Acetic acid conc. (wt. %) | Nitric acid conversion (%) | Propane conversion (%) | Mole % conversion to nitrated hydrocarbons | Mole % selectivity for nitro-methane | Mole % selectivity for 2-nitro-propane |
|---|---|---|---|---|---|---|---|---|---|---|---|
| 1A | Yes | No | 235 | 1400 | 1.35 | n/a | 87.9 | 40.6 | 57% | 2.3% | 83% |
| 1B | No | Yes | 235 | 1400 | n/a | 57.1 | 24.9 | n/a | 30% | 100% | 0% |
| 1C | Yes | Yes | 235 | 1700 | 0.47 | 57.1 | 99.7 | 47.3 | 92% | 67% | 28% |

*Examples 1A and 1B are comparative. Example 1C is inventive.

conditions: propane:nitric acid ratio of 1.35:1; nitric acid concentration of 30 wt. %; pressure of 1400 psig; residence time of 2 minute; hot oil temperature of 235° C. Acetic acid concentrations are 20 weight percent, 40 weight percent and 57 weight percent. Results are shown in Table 6.

As demonstrated in Table 6, nitromethane selectivity is observed to increase with increasing acetic acid concentration, whereas 2-nitropropane selectivity remains essentially constant.

TABLE 6

| Acetic Acid Concentration (%) | Mole % selectivity for nitro-methane | Mole % selectivity for 2-nitro-propane |
|---|---|---|
| 20 | 6.6 | 82.5 |
| 40 | 9.6 | 78.6 |
| 57 | 28.0 | 61.9 |

Example 4

Effect of Propane to Nitric Acid Mole Ratio on Nitromethane Selectivity

This Example demonstrates the effect of the propane-nitric acid mole ratio on the nitromethane selectivity. The process conditions are as follows: acetic acid concentration of 57 weight percent; nitric acid concentration of 30 wt. %; pressure of 1400-1700 psig; residence time of 90-120 sec; hot oil temperature of 235° C. Propane-nitric acid mole ratios are varied from about 0.4:1 to about 1.4:1. Results are shown in FIG. 1. As can be seen from FIG. 1, the nitromethane selectivity can be readily varied by varying the propane to nitric acid ratio. In this Example, nitromethane selectivity is shown in weight percent, calculated as follows:

Nitromethane selectivity (%)=100×g nitromethane/g nitrated hydrocarbons formed.

Example 5

Nitration of Propane/Propionic Acid

This Example demonstrates the enhancement of nitroethane selectivity in a nitrated hydrocarbon composition, through nitration of a propionic acid/propane feed. The following process conditions are used: reaction pressure of 1400 psig; hot oil temperature of 235° C.; propane-nitric acid mole ratio of 1.35:1; a nitric acid strength of 30 weight percent. The aqueous feed composition contains 30 weight percent nitric acid, 57 weight percent propionic acid, and 13 weight percent water. The results of the mass balance for the reaction are shown in Table 7.

TABLE 7

| Component | Feed (g) | Effluent (g) |
|---|---|---|
| Propane | 390 | 231 |
| Nitric Acid | 414 | 0.5 |
| Water | 178 | 269 |
| Propionic Acid | 789 | 683 |
| Acetic Acid | 0 | 40.5 |
| Acetone | 0 | 28.3 |
| Nitromethane | 0 | 7.4 |
| Nitroethane | 0 | 76.6 |
| 2-Nitropropane | 0 | 146 |
| 1-Nitropropane | 0 | 15.0 |

TABLE 7-continued

| Component | Feed (g) | Effluent (g) |
|---|---|---|
| 2,2-Dinitropropane | 0 | 2.2 |
| Nitric Oxide | 0 | 39.9 |
| Nitrous Oxide | 0 | 9.3 |
| Nitrogen | 0 | 9.3 |
| Carbon Monoxide | 0 | 15.7 |
| Carbon Dioxide | 0 | 90.5 |

Various performance metrics of the reaction are provided in Table 8.

TABLE 8

| Nitric Acid Conversion | 99.9 |
|---|---|
| Propane Conversion | 40.8 |
| Mole % conversion to nitrated hydrocarbons | 59 |
| Mole % selectivity for nitromethane | 4 |
| Mole % selectivity for nitroethane | 34 |
| Mole % selectivity for 1-nitropropane | 6 |
| Mole % selectivity for 2-nitropropane | 55 |

The results of Example 5 demonstrate the enhanced selectivity of nitroethane when using propionic acid as the co-reactant.

Example 6

Nitration of Propane/N-Butyric Acid

This Example demonstrates the enhancement of 1-nitropropane selectivity in a nitrated hydrocarbon composition, through nitration of an N-butyric acid/propane feed. The following process conditions are used: reaction pressure of 1400 psig; hot oil temperature of 220° C.; propane-nitric acid mole ratio of 0.55:1; a nitric acid strength of 30 weight percent; a residence time of 120 sec. The aqueous feed composition contains 30 wt. % nitric acid, 57.1 wt. % n-butyric acid, 12.9 wt. % water. The results of the mass balance for the reaction are shown in Table 9.

TABLE 9

| Component | Feed (g) | Effluent (g) |
|---|---|---|
| Propane | 235 | 101 |
| Nitric Acid | 306 | 11.6 |
| Water | 131 | 289 |
| Acetic Acid | 0 | 23.3 |
| n-Butyric Acid | 582 | 545 |
| Acetone | 0 | 16.8 |
| Nitromethane | 0 | 4.4 |
| Nitroethane | 0 | 10.0 |
| 2-Nitropropane | 0 | 93.2 |
| 1-Nitropropane | 0 | 95.4 |
| 2,2-Dinitropropane | 0 | 1.1 |
| Nitric Oxide | 0 | 26.9 |
| Nitrous Oxide | 0 | 7.4 |
| Nitrogen | 0 | 12.6 |
| Carbon Monoxide | 0 | 8.1 |
| Carbon Dioxide | 0 | 63.2 |

Various performance metrics of the reaction are provided in Table 10.

TABLE 10

| Nitric Acid Conversion | 96.2 |
|---|---|
| Propane Conversion | 57.2 |
| Mole % conversion to nitrated | 67 |

TABLE 10-continued

| | |
|---|---|
| hydrocarbons | |
| Mole % selectivity for nitromethane | 3 |
| Mole % selectivity for nitroethane | 6 |
| Mole % selectivity for 1-nitropropane | 46 |
| Mole % selectivity for 2-nitropropane | 45 |

The results of Example 6 demonstrate the enhanced selectivity of 1-nitropropane when using n-butyric acid as the co-reactant.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A mixed liquid-vapor phase process for making a nitrated hydrocarbon composition containing two or more compounds of formula I:

$$R-NO_2 \quad (I)$$

wherein R is independently in each compound $C_1$-$C_{12}$ hydrocarbon group optionally substituted with 1 or 2 additional $NO_2$ groups, the process comprising:
  (a) forming a reaction mixture comprising a hydrocarbon feedstock and an aqueous feed, wherein the aqueous feed comprises water, between about 10 and about 50 weight percent of nitric acid, and at least about 15 weight percent of a carboxylic acid of formula II;

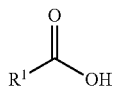

(II)

wherein $R^1$ is $C_1$-$C_{12}$ alkyl or $C_3$-$C_{12}$ cycloalkyl; and
  (b) reacting the mixture at a reaction pressure of at least 500 psi and a reaction temperature of less than about 325 degrees Celsius to provide a product stream comprising the nitrated hydrocarbon composition.

2. A process according to claim 1 wherein the product stream further comprises a carboxylic acid byproduct and at least a portion of the carboxylic acid byproduct is recycled and used as the carboxylic acid of step (a).

3. A process according to claim 1 wherein the aqueous feed comprises between about 15 and 40 weight percent of the nitric acid.

4. A process according to claim 1 wherein the aqueous feed comprises at least about 40 weight percent of the carboxylic acid of formula II.

5. A process according to claim 1 wherein the hydrocarbon feedstock is a $C_3$-$C_{12}$ alkane.

6. A process according to claim 1 wherein the hydrocarbon feedstock is propane.

7. A process according to claim 1 wherein the carboxylic acid of formula II is acetic acid.

8. A process according to claim 1 wherein the nitrated hydrocarbon composition comprises: nitromethane and 2-nitropropane.

9. A process according to claim 1 wherein the reaction is conducted in a downflow configured reactor.

10. A mixed liquid-vapor phase process for making a nitrated hydrocarbon composition, the process comprising:
  (a) forming a reaction mixture comprising propane and an aqueous feed comprising water, between about 10 and about 50 weight percent of nitric acid, and at least about 15 weight percent of acetic acid; and
  (b) reacting the mixture at a pressure of at least about 1000 psi and a temperature of between about 180 and about 325 degrees Celsius to provide a product stream comprising the nitrated hydrocarbon composition.

* * * * *